United States Patent
Traboulsi et al.

(10) Patent No.: US 9,403,624 B2
(45) Date of Patent: Aug. 2, 2016

(54) DEVICE AND METHOD FOR DISPENSING A BEVERAGE AND IMAGING CONTRAST AGENT

(75) Inventors: Maeghan E. Traboulsi, South Boston, MA (US); Peter Quagliano, Richmond, VA (US)

(73) Assignee: Beekley Corporation, Bristol, CT (US)

( * ) Notice: Subject to any disclaimer, the term of this patent is extended or adjusted under 35 U.S.C. 154(b) by 25 days.

(21) Appl. No.: 12/862,675

(22) Filed: Aug. 24, 2010

(65) Prior Publication Data

US 2011/0042255 A1 Feb. 24, 2011

Related U.S. Application Data

(60) Provisional application No. 61/236,394, filed on Aug. 24, 2009.

(51) Int. Cl.
    | | |
    |---|---|
    | *B65D 85/00* | (2006.01) |
    | *B65D 23/00* | (2006.01) |
    | *B65D 25/56* | (2006.01) |
    | *G01F 19/00* | (2006.01) |

(52) U.S. Cl.
    CPC ............... *B65D 23/00* (2013.01); *B65D 25/56* (2013.01); *G01F 19/00* (2013.01)

(58) Field of Classification Search
    USPC ........ 206/534, 459.5; 220/662, 663; 215/388, 215/365, 366; 40/310; 73/426
    See application file for complete search history.

(56) References Cited

U.S. PATENT DOCUMENTS

| | | | |
|---|---|---|---|
| RE7,606 E | | 4/1877 | Boggs |
| 1,744,328 A | * | 1/1930 | Morley ........................ 215/383 |
| 2,294,473 A | * | 9/1942 | Makeley .................... 229/162.2 |
| 3,517,450 A | * | 6/1970 | Greco ............................. 40/310 |
| 4,085,866 A | * | 4/1978 | Fekl .............................. 222/158 |
| 5,021,220 A | | 6/1991 | Mertens |
| 5,046,609 A | * | 9/1991 | Mangini et al. ............... 206/232 |
| 5,244,096 A | | 9/1993 | Stoner |
| 5,260,049 A | | 11/1993 | Illig et al. |
| 5,350,612 A | * | 9/1994 | Stern et al. ................... 428/40.5 |
| 5,405,600 A | | 4/1995 | Illig et al. |
| 5,496,535 A | | 3/1996 | Kirkland |
| 5,529,189 A | | 6/1996 | Feldschuh |
| 5,896,990 A | | 4/1999 | Barzana |
| 6,036,017 A | * | 3/2000 | Bayliss, IV ................... 206/534 |

(Continued)

OTHER PUBLICATIONS

JCAHO Medication Management Standards, 4.3 MM.

*Primary Examiner* — David Fidei
(74) *Attorney, Agent, or Firm* — McCarter & English, LLP (57) ABSTRACT

A device and method are provided for storing a prefilled liquid beverage, receiving an oral contrast imaging agent that is mixed with the prefilled liquid beverage, and dispensing a resulting beverage/oral contrast imaging agent mixture. The device has a body defining a chamber for storing the prefilled liquid beverage. A closure is movable between a closed position for sealing the prefilled liquid in the chamber, and an open position for (i) introducing the oral contrast imaging agent into the chamber for mixture with the prefilled liquid beverage, and (ii) dispensing the beverage/oral contrast imaging agent mixture. The device may include first graduations, a time scale and second graduations. The body defines a substantially smooth, axially extending patient information surface including thereon a plurality of marking spaces and respective patient information indicia associated with each marking space for marking thereon information relating to a respective patient.

35 Claims, 3 Drawing Sheets

(56) References Cited

U.S. PATENT DOCUMENTS

| | | | |
|---|---|---|---|
| 6,082,777 A * | 7/2000 | Grosskopf et al. | 283/81 |
| 6,179,125 B1 * | 1/2001 | Kvitrud et al. | 206/459.1 |
| 6,252,494 B1 | 6/2001 | Howell | |
| 6,254,294 B1 | 7/2001 | Muhar | |
| 6,581,773 B2 | 6/2003 | Kaplan | |
| 6,692,515 B2 | 2/2004 | Boehm, Jr. et al. | |
| 6,793,075 B1 | 9/2004 | Jeter | |
| 6,800,273 B2 | 10/2004 | Rajopadhye | |
| 6,837,376 B2 | 1/2005 | Pauli | |
| 6,976,628 B2 * | 12/2005 | Krupa | 235/462.08 |
| 7,014,066 B2 | 3/2006 | Jeter | |
| 7,935,100 B2 * | 5/2011 | Janus | 604/404 |
| 2002/0086812 A1 | 7/2002 | Schweinfest | |
| 2004/0129581 A1 | 7/2004 | Tompkins | |
| 2004/0228799 A1 | 11/2004 | Armstrong | |
| 2005/0180920 A1 | 8/2005 | Giuliano | |
| 2005/0236296 A1 | 10/2005 | Horkins et al. | |
| 2006/0006134 A1 * | 1/2006 | Luo | 215/388 |
| 2006/0034873 A1 | 2/2006 | Radke | |
| 2006/0140864 A1 | 6/2006 | Raines | |
| 2006/0180566 A1 | 8/2006 | Mataya | |
| 2007/0062277 A1 * | 3/2007 | Miller | 73/428 |

* cited by examiner

DEVICE AND METHOD FOR DISPENSING A BEVERAGE AND IMAGING CONTRAST AGENT

CROSS-REFERENCE TO RELATED APPLICATIONS

This application claims priority to U.S. Provisional Application No. 61/236,394, filed Aug. 24, 2009, the contents of which are hereby incorporated by reference in their entirety as part of the present disclosure.

FIELD OF THE INVENTION

The present invention relates to devices and methods for administering oral contrast agents for X-ray, CT and MR imaging, and more particularly, to devices and methods for mixing oral contrast agents with flavored beverages, and administering predetermined amounts of the mixtures within predetermined time intervals before imaging.

BACKGROUND INFORMATION

There are a variety of imaging techniques that have been used to diagnose disease in humans. One of the first techniques employed was X-rays. In X-rays, the images of the patients' body reflect the different densities of body structures. To improve the diagnostic utility of this imaging technique, contrast agents are employed to increase the density difference between various structures, such as between the gastrointestinal tract and its surrounding tissues. Barium sulfate and iodinated contrast media are the two primary pharmaceutical oral contrast agents used for X-ray gastrointestinal studies to visualize the esophagus, stomach, small intestine, and large intestine. Likewise, these same contrast agents are used for X-ray-based CT images to improve visualization and distension of the gastrointestinal tract and to provide improved contrast between the gastrointestinal tract and the structures adjacent to it, such as the blood vessels and lymph nodes. Such gastrointestinal oral contrast agents increase the density inside the esophagus, stomach, small intestine, and large intestine, and allow differentiation of the gastrointestinal system from the surrounding structures. Such gastrointestinal oral contrast agents also distend the bowel lumen allowing better evaluation of bowel wall structures, including abnormalities such as wall thickening or luminal obstruction.

Magnetic resonance imaging is another imaging technique; however, unlike X-rays and CT, MR does not utilize ionizing radiation. MR employs a magnetic field, radiofrequency energy and magnetic field gradients to make images of the body. The contrast or signal intensity differences between tissues mainly reflect the T1 and T2 relaxation values and the proton density of the tissues. Like CT, MR can make cross-sectional images of the body and it is desirable for many MR scans that a gastrointestinal contrast agent be administered to allow differentiation of the gastrointestinal system from the surrounding structures. Such gastrointestinal oral contrast agents also distend the bowel lumen allowing better evaluation of bowel wall structures, including abnormalities such as wall thickening or luminal obstruction.

Opacification of the gastrointestinal tract is a routine part of patient preparation prior to CT examination of the abdomen and pelvis because proper filling and distention of the bowel lumen with contrast medium facilitates identification of the normal and abnormal anatomy. For this reason, oral contrast agents are administered to the vast majority of patients undergoing CT scans of the abdomen and pelvis. Less commonly, oral contrast agents are administered to patients undergoing MR scans of the abdomen and pelvis.

In the early 1980s, when CT scan imaging was first gaining widespread use, the first oral agents used were the ionic iodinated contrast agents, comprised of the iodine-containing salts sodium diatrizoate, meglumine diatrizoate, or mixtures thereof. One example of the ionic iodinated oral contrast agents is Gastrografin® (Bracco Diagnostics, Princeton, N.J.), which is composed of the iodine-containing salts meglumine diatrizoate and sodium diatrizoate. Pharmaceutical agents like Gastrografin® were already approved for oral use and were widely used in full strength concentration for diagnostic gastrointestinal radiology imaging. These products, as well as the newer non-ionic iodinated agent approved for oral administration in the United States (e.g., iohexol, trade name Omnipaque®, GE Healthcare, Princeton, N.J.), were too concentrated in the form supplied by the manufacturers to be used for gastrointestinal opacification during CT imaging. These products were, therefore, diluted with water or other beverages in order to be of the proper concentration for optimal CT scan imaging.

Similarly, the gadolinium-based oral contrast agents, such as gadopentetate dimeglumine, are too concentrated in the form supplied by the manufacturers to be used for gastrointestinal opacification during MR imaging. These products must be diluted with water or other beverage in order to be of the proper concentration for optimal gastrointestinal opacification during MR imaging.

In addition to dilution for imaging, oral contrast agents are mixed with beverages to improve palatability and taste. Due to the bitter and unpleasant taste of oral contrast agents, and the relatively large volume of liquid that must be consumed, many patients have difficulty drinking an oral contrast agent unless it is mixed with a beverage that masks the unpleasant taste. Soda, fruit juices, flavored water or powdered drink mixes such as Kool-Aid™ or Crystal Light™ have been mixed with oral contrast agents to improve palatability and taste. In some cases, the beverage is poured, or in the case of powdered drink mixes combined with water, in a pitcher or similar container. The oral contrast agent is then added to the beverage in the pitcher and dispensed in a cup to the patient. The pitcher may contain the diluted oral contrast for a single patient or for multiple patients.

Using a pitcher and dispensing the oral contrast agent in a cup results in difficulty in monitoring and ensuring that the patient consumes the desired quantity of oral contrast agent over the time period established, particularly if the pitcher is used for oral contrast agent for more than one patient. It is also difficult to provide labeling or means to write on the pitcher the dose or type of oral contrast used, the patient name and medical identification number, and other data that may be of medical or regulatory significance.

In other cases, the dilute oral contrast agent is mixed and dispensed in a series of cups Because typically 32 ounces or more of the dilute oral contrast agent must be consumed by the patient, multiple cups are required. The use of multiple cups of oral contrast agent results in difficulty in monitoring the rate of consumption. In addition, labeling of the cups is typically minimal, and in some cases no labeling is used at all.

Accordingly, it would be advantageous to have a container or other device for administration of oral contrast agent that allowed the user to obtain the proper concentration and dilution of the oral contrast agent, monitor consumption of the oral contrast agent to ensure that proper quantities are consumed within the time period established, and/or provide easy labeling to track information such as the patient name, oral contrast agent used, concentration of oral contrast agent in the container, date and time of preparation, and quantities to be consumed for specific time periods.

SUMMARY OF THE INVENTION

In accordance with a first aspect, the present invention is directed to a device for storing a beverage, receiving an oral contrast imaging agent that is mixed with the beverage, and dispensing a resulting beverage/oral contrast imaging agent mixture. The device comprises a body defining a chamber for receiving the beverage. A closure is movable between a closed position for sealing the chamber, and an open position for (i) introducing the oral contrast imaging agent into the chamber for mixture with a beverage, and/or (ii) dispensing the beverage/oral contrast imaging agent mixture. A liquid volume scale is located on the body and includes a plurality of axially spaced first graduations. Each first graduation is indicative of a respective volume of liquid in the chamber. A time scale is located on the body and includes a plurality of axially spaced second graduations. Each second graduation is (i) indicative of an approximate time at which a user should consume a volume of beverage/oral contrast imaging agent mixture corresponding to a respective first graduation, and/or (ii) adjacent to or overlying a space for marking thereon an approximate time at which a user should consume a volume of beverage/oral contrast imaging agent mixture corresponding to a respective first graduation.

In some embodiments of the present invention, the body includes an external wall defining a substantially transparent portion allowing a user to view a liquid within the chamber and determine (i) a volume of liquid in the chamber, and/or (ii) a volume of liquid dispensed from the chamber, based on the liquid volume scale. In some such embodiments, the substantially transparent portion is an axially or longitudinally-extending window located adjacent to the liquid volume scale. In some such embodiments, a label, such as a transparent shrink-wrap label, defines the axially or longitudinally-extending window.

In some embodiments of the present invention, each second graduation of the time scale is a laterally extending line located adjacent to a respective first graduation. The device further includes a marking surface located adjacent to each line to allow marking thereon with a writing instrument a respective time approximately at or before which a user should consume a volume of liquid corresponding to a respective first graduation.

The currently preferred embodiments of the present invention preferably define a substantially smooth, axially extending patient information surface including thereon a plurality of marking spaces and respective patient information indicia associated with each marking space for marking thereon information relating to a respective patient. In some such embodiments, the patient information indicia relates to at least a plurality of the following: patient name, patient identification number or alphanumeric indicia, patient room number, oral contrast imaging agent added to the beverage (including lot number and expiration date), volume of oral contrast imaging agent added to the beverage, the date and/or time the beverage and oral contrast imaging agent were mixed, the person that prepared the mixture, and device number (e.g., 1, 2, 3, or A, B, C, etc.) when more than one beverage/oral contrast imaging agent-containing device is to be consumed by the patient in a particular temporal sequence.

Some embodiments of the present invention further comprise a separate patient information label that is attachable to the body, is defined by a substantially flat sheet that allows a user to place the label on a substantially flat surface and write thereon, and that includes thereon a plurality of marking spaces and respective patient information indicia associated with each marking space for writing thereon information relating to a respective patient. In some such embodiments, the patient information indicia relates to at least a plurality of the following: patient name, patient identification number or alphanumeric indicia, patient room number, oral contrast imaging agent added to the beverage (including lot number and expiration date), volume of oral contrast imaging agent added to the beverage, the date and/or time the beverage and oral contrast imaging agent were mixed, the person that prepared the mixture, and device number (e.g., 1, 2, 3, or A, B, C, etc.) when more than one beverage/oral contrast imaging agent-containing device is to be consumed by the patient in a particular temporal sequence. Preferably, the patient information label is substantially the same size and shape as the patient information surface on the body of the device for substantially entirely covering the patient information surface when attached thereto.

In accordance with another aspect, the present invention is directed to a device for storing a beverage, receiving an oral contrast imaging agent that is mixed with the beverage, and dispensing a resulting beverage/oral contrast imaging agent mixture. The device comprises first means for forming a chamber and receiving therein a beverage; and second means movable between a closed position for sealing the chamber, and an open position for (i) introducing an oral contrast imaging agent into the chamber for mixture with a beverage in the chamber, and/or (ii) dispensing a beverage/oral contrast imaging agent mixture. A plurality of third means are axially spaced relative to each other for indicating a respective volume of a beverage/oral contrast imaging agent mixture in the chamber. A plurality of fourth means are axially spaced relative to each other adjacent to respective third means (i) for indicating an approximate time at which a user should consume a respective volume of a beverage/oral contrast imaging agent mixture in the chamber based on at least one third means, and/or (ii) for marking thereon or adjacent thereto an approximate time at which a user should consume a respective volume of a beverage/oral contrast imaging agent mixture in the chamber based on at least one third means.

In the currently preferred embodiments of the present invention, the first means is a body, the second means is a closure, each third means is a graduation of a liquid volume scale, and each fourth means is a graduation of a time scale.

In accordance with another aspect, the present invention is directed to a method comprising the following steps:

providing a device with a chamber and a beverage within the chamber;

adding a predetermined amount of a water soluble oral contrast imaging agent to the beverage within the chamber;

mixing the beverage and oral contrast imaging agent within the chamber to form a beverage/oral contrast imaging agent mixture; and administering to a person predetermined amounts of the beverage/oral contrast imaging agent mixture at predetermined time intervals in accordance with a time scale located on an externally visible surface of the device.

In some embodiments of the present invention, the method further comprises the step of marking the time scale at each of a plurality of graduations located on an externally visible surface of the device with respective times. Each marked graduation indicates an approximate amount of the beverage/oral contrast imaging agent mixture to be consumed by a respective approximate time.

The currently preferred embodiments of the present invention further comprise the steps of providing a device including a liquid volume scale appearing on an externally visible surface of the device including a plurality of spaced liquid volume graduations, and marking each time adjacent to a respective liquid volume graduation to indicate (i) the mixture volume to be administered approximately by expiration of the respective time, (ii) the total mixture volume to be administered approximately by expiration of the respective time, and/or (iii) the mixture volume remaining in the chamber approximately by expiration of the respective time.

Currently preferred embodiments of the present invention further comprise the steps of providing a body defining a substantially smooth, axially extending patient information surface including thereon a plurality of marking spaces and respective patient information indicia associated with each marking space, and marking thereon information relating to a respective patient.

One advantage of the present invention, and/or of the currently preferred embodiments thereof, is that they allow a user to monitor consumption of the oral contrast agent to ensure that proper quantities are consumed within the time period established, and/or provide easy labeling to track information such as the patient name, oral contrast agent used, concentration of oral contrast agent in the device, and quantities to be consumed for specific time periods.

Other objects and advantages of the present invention, and/or of the currently preferred embodiments thereof, will be come more readily apparent in view of the following detailed description of the currently preferred embodiments and accompanying drawings.

DETAILED DESCRIPTION OF THE CURRENTLY PREFERRED EMBODIMENTS

Figure 1:
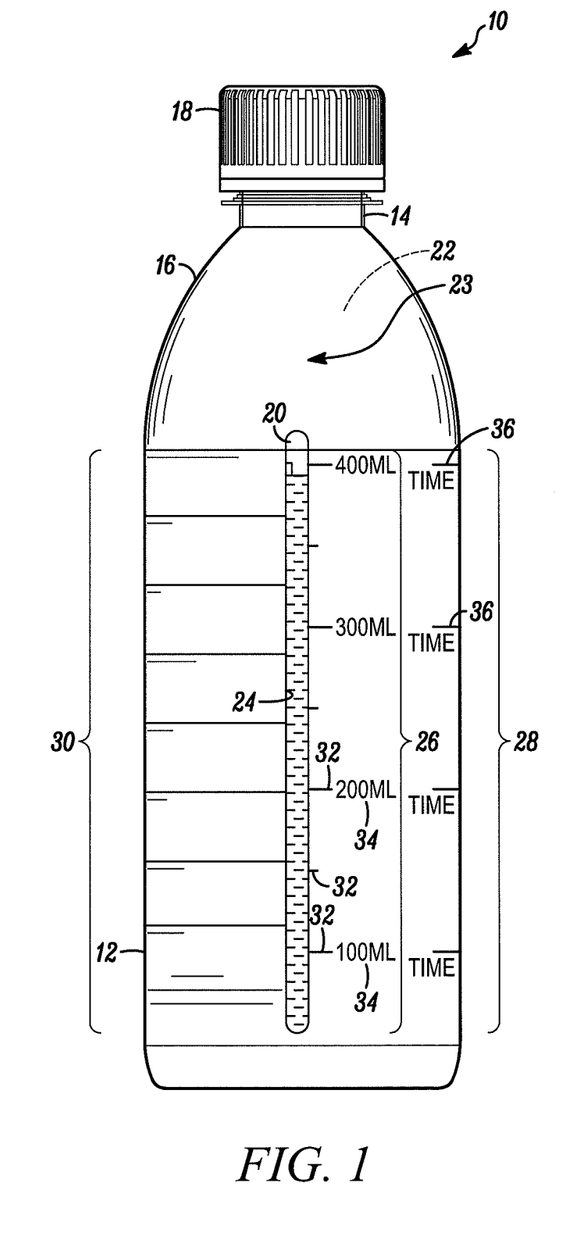
FIG. 1 is a side elevational view of a container embodying the present invention containing a prefilled volume of flavored beverage that is adapted to receive an oral contrast agent that is mixed with the flavored beverage to form a beverage/contrast agent mixture, and that includes a volume scale and a time scale on an externally visible surface for identifying the amount of mixture that should be consumed approximately on or before expiration of each respective time interval.

In FIG. 1, a device embodying the present invention is indicated generally by the reference number 10. The device 10 is a container in the form of a plastic bottle defining a substantially cylindrical body 12, a neck 14 at the top of the bottle, and a curvilinear shoulder 16 extending between the cylindrical body and neck. A closure in the form of a threaded cap 18 is threadedly connected to the neck 14 to seal the bottle. The interior of the bottle defines a fluid receiving chamber 20. The chamber 20 is prefilled with a flavored beverage adapted for mixture with an oral contrast imaging agent, such as a water soluble oral contrast imaging agent. In the currently preferred embodiments of the present invention, the flavored beverage is of the type disclosed in U.S. patent application Ser. No. 12/478,794, filed on Jun. 5, 2009, entitled "Palatable Liquid Dilution Vehicles for Oral Contrast Agents", which is hereby incorporated by reference in its entirety as part of the present disclosure. However, as may be recognized by those of ordinary skill in the pertinent art based on the teachings herein, the beverage may take the form of any of numerous different beverages that are currently known, or that later become known, and that are suitable for mixture with an oral contrast imaging agent, such as water, flavored beverages, and non-flavored beverages. As shown typically in FIG. 1, when the container 10 is prefilled with a beverage the chamber 20 defines an empty head space 22 extending between the prefilled beverage and the neck 14.

The container 10 includes a label 23. In the illustrated embodiment, the label 23 is a shrink-wrap label that covers substantially the entire body 12 and shoulder 14 of the container 10. The label 23 defines a longitudinally-extending, substantially transparent window 24. In the illustrated embodiment, the window 24 is defined either by a narrow, elongated slot formed in the label or by a narrow, elongated, substantially transparent portion of the label. The container 10 further includes a liquid volume scale 26 located on one side of the transparent window 24, a time scale 28 laterally spaced adjacent to the liquid volume scale 26, and a patient information section 30 located on an opposite side of the window 24 relative to the volume and time scales 26 and 28, respectively.

As shown in FIG. 1, the liquid volume scale 26 includes a plurality of liquid volume graduations 32 that are axially spaced relative to each other at predetermined distances adjacent to the elongated window 24. As can be seen, a plurality of the liquid volume graduations 32 are marked with respective numerical indicia 34 located adjacent to the graduation to indicate a respective volume of liquid within the chamber 20. A plurality of unmarked liquid graduations 32 are substantially equally between adjacent marked liquid graduations 32. In the illustrated embodiment, the indicia 34 indicate the volume of liquid remaining in the chamber 20 at the level of the respective marked liquid volume graduations 32. In the illustrated embodiment, the unmarked graduations 32 are axially spaced approximately half way between adjacent marked graduations. Therefore, a user can easily determine the volume at the unmarked graduations based on the volumes of the adjacent marked graduations. In the illustrated embodiment, the marked liquid volume graduations 32 are spaced a distance equal to approximately 100 ml relative to each other. Accordingly, in the illustrated embodiment, the highest marked indicia 34 indicates that approximately 400 ml of liquid remains in the chamber at the level of the respective marked liquid volume indicia 32, the next marked indicia 34 indicates that approximately 300 ml of liquid remains in the chamber at the level of the respective marked liquid volume indicia 32, the next marked indicia 34 indicates that approximately 200 ml of liquid remains in the chamber at the level of the respective marked liquid volume indicia 32, and the next marked indicia 34 indicates that approximately 100 ml of liquid remains in the chamber at the level of the respective marked liquid volume indicia 32. Each unmarked liquid volume indicia 32 marks a volume that is 50 ml less than or greater than the adjacent upper and lower marked indicia 32, respectively. As may be recognized by those of ordinary skill in the pertinent art based on the teachings herein, the liquid volume scale may include any of numerous different graduations and/or different types of graduations, any of numerous different types of indicia for marking the graduations, and may include any desired number of graduations with our without associated indicia. In addition, the indicia may indicate any of numerous different types of information, such as the volume of liquid remaining at the respective level, the volume of liquid between adjacent indicia or other indicia, and/or the volume of liquid consumed when the level of liquid is at or near the level of the respective graduation.

The time scale 28 is laterally spaced adjacent to the volume scale 26 and includes a plurality of time graduations 36 that are axially spaced relative to each other. In the illustrated embodiment, each time graduation 36 is laterally aligned with a respective liquid volume graduation 32 and liquid volume indicia 34 and includes a blank space over the graduation and the word "time" printed adjacent to the graduation and the blank space. The user, such as a medical or pharmaceutical technician, marks the blank space with the approximate time by which the patient should consume the liquid beverage/contrast agent mixture to the level of the respective graduation 32 on the liquid volume scale 26. Accordingly, in the illustrated embodiment, the technician marks that time scale to indicate at the uppermost graduation 36 the approximate time by which the volume of liquid in the chamber should be at the 400 ml level, marks the next lower graduation 36 to indicate the approximate time by which the volume of liquid in the chamber should be at the 300 ml level, marks the next lower graduation 36 to indicate the approximate time by which the volume of liquid in the chamber should be at the 200 ml level, marks the next lower graduation 36 to indicate the approximate time by which the volume of liquid in the chamber should be at the 100 ml level, and marks the space below the next lower graduation 36 to indicate the approximate time by which the volume of liquid in the chamber should be substantially entirely consumed. As may be recognized by those of ordinary skill in the pertinent art based on the teachings herein, the time scale may take any of numerous different configurations that are currently known, or that later become known. For example, the time scale may include any desired number of time graduations, or may include time graduations pre-marked with respective times and/or time intervals at which the respective volumes of liquid in the chamber should be consumed. Further, the graduations of the time and volume scales may take the form of substantially horizontally extending lines as shown, or may take any of numerous other configurations that are currently known, or that later become known.

The patient information section 30 includes a plurality of blank boxes and associated indicia printed within or adjacent to the box to indicate the information that should be written or otherwise marked in the box. In the illustrated embodiment, the patient information boxes include indicia for indicating the following information: patient name, patient identification number or alphanumeric indicia, patient room number, contrast agent added to the beverage, volume of contrast agent added to the beverage, the date and/or time the beverage and contrast agent were mixed, the person, such as the technician, that prepared the mixture and the device number. The device number may be any indicator (1, 2, 3, etc. or A, B, C, etc) chosen to inform the patient and/or technician of the proper sequence when more than one beverage/oral contrast imaging agent-containing device is to be consumed by the patient in a particular temporal sequence. However, as may be recognized by those of ordinary skill in the pertinent art based on the teachings herein, this listing of patient information is only exemplary, and the patient information section 30 may include any of numerous different types of information that is desired or otherwise required, and that is currently known, or that later becomes known.

Figure 2:
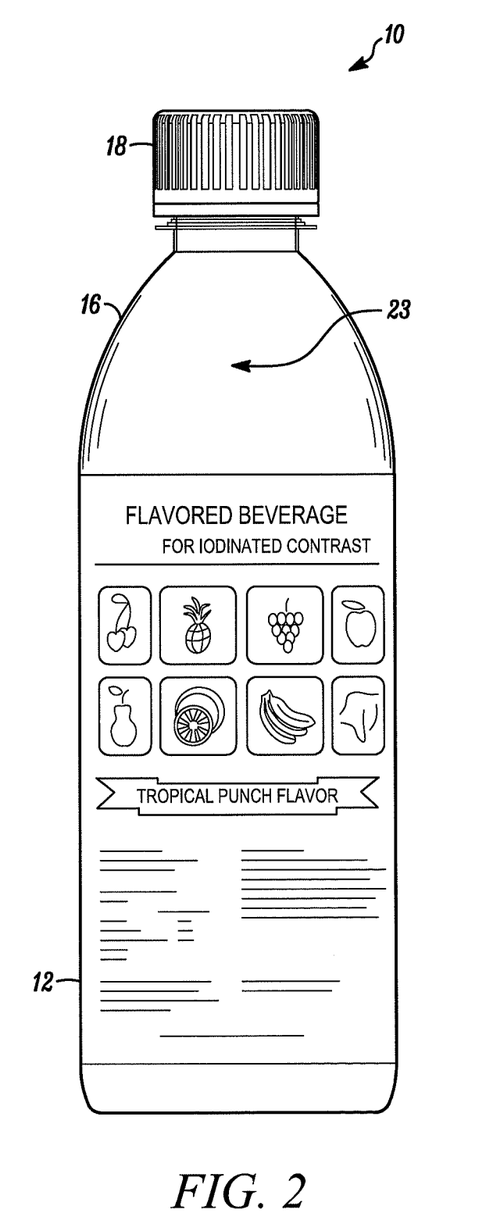
FIG. 2 is an opposite side elevational view of the container of FIG. 1.

As shown in FIGS. 1 and 2, the body 12 of the container defines a longitudinally extending, substantially smooth surface underlying the patient information section 30 and the time scale 28. In the illustrated embodiment, the longitudinally extending, substantially smooth surface is defined by the cylindrical shaped body 12. One advantage of this feature is that it facilitates the ability of a technician or other user to mark or otherwise write the required or otherwise desired information in the patient information section and on the time scale. As may be recognized by those of ordinary skill in the pertinent art based on the teachings herein, the body of the container or other device may take any of numerous different shapes and/or configurations that are currently known, or that later become known, and thus the longitudinally extending, substantially smooth surface underlying the time scale and/or the patient information section may be defined by any of numerous different structures of the container or other device that are currently known, or that later become known.

As shown in FIG. 2, the side of the label 23 opposite the window 24, liquid volume scale 26, and time scale 28 may include conventional information such as branding information, product ingredients, and/or any other required or otherwise desired labeling information.

Figure 3:
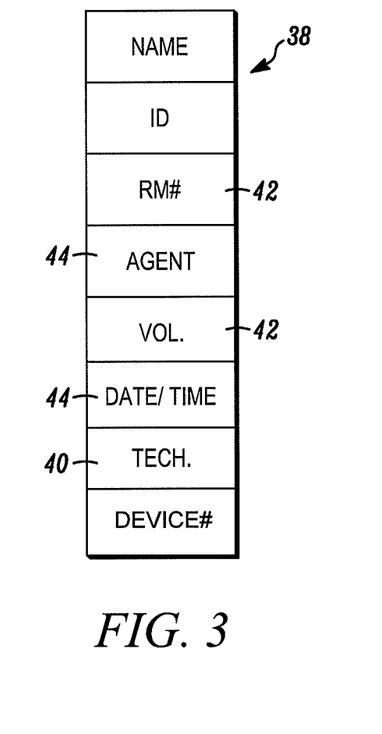
FIG. 3 is a top plan view of a separate patient information label that can be placed on a flat surface for writing or otherwise marking the patient information on the label, and then attached to the label of the container of FIG. 1 superimposed over the patient information section on the container.

Turning to FIG. 3, in an alternative embodiment, the device 10 further includes a separate patient information label 38 that is attachable to the external wall of the body 12, such as to the shrink-wrap label 23, and is defined by a substantially flat sheet 40 allowing a user to place the label on a substantially flat surface and write thereon. The separate patient label 38 includes thereon a plurality of blank spaces, shown typically at 42, and respective patient information indicia associated with each blank space for writing thereon identification information concerning a patient who will consume the beverage/oral contrast imaging agent. In the illustrated embodiment, the patient information spaces 42 include respective indicia, shown typically at 44, for indicating the following information: patient name, patient identification number or alphanumeric indicia, patient room number, contrast agent added to the beverage, volume of contrast agent added to the beverage, the date and/or time the beverage and contrast agent were mixed, and the person, such as the technician, that prepared the mixture. However, as may be recognized by those of ordinary skill in the pertinent art based on the teachings herein, this listing of patient information is only exemplary, and the separate patient information label may include any of numerous different types of information that is desired or otherwise required, and that is currently known, or that later becomes known.

Also in the illustrated embodiment, the separate patient information label 38 is substantially the same size and shape as the patient information section 30 on the label cover 23 for substantially entirely covering the patient information surface when attached thereto. In the currently preferred embodiment, the separate patient information label 38 is adhesively backed with a pressure sensitive adhesive for attachment to the label cover 23 in a position superimposed on or otherwise overlying the patient information section 30 to cover that surface (but not the window, and preferably not any other information bearing surfaces of the cover). In one exemplary embodiment, a plurality of such labels are provided in sheet form, wherein the top side of the sheet includes a plurality of labels printed thereon and separated by perforated lines or other frangible portions therebetween that are formed in the sheet to allow the individual labels to be manually separated from the sheet, an adhesive layer on the underside of the sheet for adhesively attaching each label to a respective container or other device, and a releasable backing releasably attached to the adhesive-backed side of the sheet. In another exemplary embodiment, the adhesive-backed labels and releasable backings are provided in roll form. Accordingly, as may be recognized by those of ordinary skill in the pertinent art based on the teachings herein, the separate patient information labels may be provided in any of numerous different forms and/or configurations that are currently known, or that later become known.

In the use of the device 10, the chamber 22 of each container 10 is prefilled with a predetermined volume of flavored beverage that is sealed within the container by the closure 18. The user, such as a technician, removes the cap 18 to open the container, introduces a predetermined amount of oral contrast imaging agent through the opening and into the chamber 20, closes the cap 18 to reseal the container, and by shaking or other means mixes the beverage and oral contrast imaging agent into a resulting beverage/oral contrast imaging agent mixture. As indicated above, each prefilled container 10 defines a predetermined head space 22 (indicated in phantom lines) that allows sufficient space to introduce the predetermined volume or amount of oral contrast imaging agent into the chamber without overflowing the chamber and/or otherwise to provide sufficient space to conveniently mix the agent with the beverage. Prior to or after mixture of the beverage and agent, the user, such as the technician, fills in the patient information section 30 and the time scale 28. In the time scale 28, the user indicates the approximate times at which the respective volumes of beverage/agent mixture as indicated by the volume scale 26 should be ingested by the patient. The patient may then consume the beverage/contrast agent mixture in accordance with the volume and time scales 26 and 28, respectively. The window 24 allows the user and/or patient to monitor the level of beverage/contrast agent mixture in the chamber 20 and ensure that the patient consumes the appropriate volume at or prior to expiration of each respective time or time value as indicated by the volume and time scales. If necessary, the patient may consume several containers, or each container may be sized to hold a sufficient volume of beverage/contrast agent for a complete single patient procedure. In the currently preferred embodiments of the present invention a straw (not shown) is inserted through the opening of the container and used to drink the beverage/contrast agent mixture. However, if desired, the patient can drink directly from the opening in the container rather than use a straw. As may be recognized by those of ordinary skill in the pertinent art based on the teachings herein, the container may include any of numerous different types of closures, spouts, nozzles, dispensing tips or other devices to facilitate dispensing and/or drinking the beverage/contrast agent mixture.

As may be recognized by those of ordinary skill in the pertinent art based on the teachings herein, numerous changes and modifications may be made to the above-described and other embodiments of the present invention without departing from the scope of the invention. For example, the device may take the form of a bottle as illustrated, or may take the form of any of numerous other devices defining chambers for receiving beverages and contrast agents. The containers or other devices may be made of any of numerous different types of plastics that are currently known or that later become known, and/or may be made of any of numerous different materials that are currently known or that later become known, such as any of numerous different types of glass or recycled materials. Similarly, the label covering the container or other device may take the form of any of numerous different types of labels that are currently known, or that later become known, and/or the label may cover only a discrete portion or portions of the device, the device may include a plurality of such labels, or the device may not include any such label. For instance, the device itself may have printed or otherwise formed thereon the various features of the preferred embodiments of the invention. The volume scale and/or the time scale likewise can take the form of any of numerous different types of scales that are currently known or that later become known. For example, the time scale may or may not have times or time values pre-marked or otherwise appearing thereon. Similarly, the volume scale need not include any volume markings or indicia adjacent to respective graduations. The graduations of either scale may or may not be evenly or uniformly spaced. The graduations may be defined by any of numerous different markings or indicia, and different graduations may be defined by any of numerous different markings or indicia, that are currently known, or that later become known. The patient information section likewise can include indicia and/or blank spaces or other marking surfaces for receiving any of numerous different types of information that are currently known or desired for such applications, or different information. In addition, the container or other device may not be prefilled with a flavored beverage or other type of liquid; rather, the container or other device may be provided empty and the user may fill the container with the beverage and the contrast imaging agent, or the container or other device may be provided with a dry powdered version or concentrated liquid version of the beverage requiring reconstitution with water or other liquid prior to or after the addition of the oral contrast agent. The beverage and oral imaging contrast agent similarly may take the form of any of numerous different beverages and/or contrast agents for any of numerous different imaging modalities, that are currently known, or that later become known. Accordingly, this detailed description of the currently preferred embodiments is to be taken in an illustrative as opposed to a limiting sense.

What is claimed is:

1. A device for storing a beverage, receiving an oral contrast imaging agent that is mixed with the beverage, and dispensing a resulting mixture, the device comprising:
    a body defining a chamber and an orally-engageable opening to the chamber, the body containing a liquid filled to a first level within the chamber, and a predetermined volume of head space above the first level for receiving a predetermined volume of oral contrast imaging agent for mixture with the liquid within the chamber, thereby filling the chamber to a second level and forming the resultant mixture of liquid prior to consumption thereof by a user, wherein the predetermined volume of head space is configured so that the predetermined volume of oral contrast imaging agent provides a proper concentration in the resultant mixture of liquid for imaging;
    a closure movable between a closed position configured to close the orally-engageable opening and seal the chamber, and an open position configured to at least one of (i) introduce an oral contrast imaging agent into the chamber through the orally-engageable opening for mixture with a beverage, and (ii) allow a user to engage the orally engageable opening and consume the mixture from the chamber through the opening, and thereby dispense the mixture;
    a first marking located on the body below the second level and indicating a third level within the chamber below said second level, the marking further comprising (i) a first time or (ii) a first time interval, by which a user should consume the liquid through the orally-engageable opening to the indicated third level within the chamber; and
    a second marking located on the body below the first marking and indicating a fourth level within the chamber below said third level, the second marking further comprising (i) a second time later than the first time or (ii) a second time interval, by which a user should consume the liquid through the orally-engageable opening to the indicated fourth level within the chamber, wherein said first marking is located closer to the orally-engageable opening than said second marking.

2. A device as defined in claim 1, wherein the device further comprises a liquid volume scale located on the body comprising a plurality of axially spaced volume graduations, wherein each volume graduation indicates a volume of liquid in the chamber.

3. A device as defined in claim 2, wherein the body includes an external wall defining a substantially transparent portion allowing a user to view the liquid within the chamber and determine at least one of (i) a volume of liquid in the chamber, or (ii) a volume of liquid dispensed from the chamber, based on the liquid volume scale.

4. A device as defined in claim 3, wherein the substantially transparent portion is an axially-extending window located adjacent to the liquid volume scale.

5. A device as defined in claim 2, wherein each volume graduation is indicative of a respective volume of liquid remaining in the chamber at the level of the respective volume graduation.

6. A device as defined in claim 2, wherein adjacent volume graduations are axially spaced relative to each other a predetermined distance corresponding to a liquid volume within the range of about 25 ml to about 75 ml.

7. A device as defined in claim 2, wherein each of a plurality of volume graduations includes a respective number adjacent thereto indicative of at least one of (i) a volume of liquid in the chamber, (ii) a volume of liquid dispensed from the chamber, or (iii) a volume of liquid to be ingested by a patient approximately by a respective time or within a respective time interval indicated by the at least one marking.

8. A device as defined in claim 1, wherein the device further comprises a time scale located on the body comprising a plurality of axially spaced time graduations, wherein each time graduation corresponds to a volume of liquid in the chamber, and wherein the first marking and the second marking each define a time graduation of the time scale.

9. A device as defined in claim 8, further comprising a liquid volume scale located on the body, comprising a plurality of axially spaced volume graduations indicating a volume of liquid in the chamber.

10. A device as defined in claim 9, wherein the time graduations are laterally aligned with a respective volume graduation.

11. A device as defined in claim 9, wherein each time graduation is a laterally extending line located adjacent to a respective volume graduation, and the device further includes a marking surface located adjacent to each line configured for marking thereon with a writing instrument a respective time approximately at or before which a user should consume a volume of liquid corresponding to a respective volume graduation.

12. A device as defined in claim 8, wherein the body defines a substantially smooth, axially-extending surface underlying the time scale that provides a relatively firm surface configured for writing on or adjacent to the time scale.

13. A device as defined in claim 12, wherein the substantially smooth, axially extending surface extends substantially throughout a length of the time scale.

14. A device as defined in claim 9, wherein the device includes a label secured to the external wall, and the label includes printed thereon at least one of the liquid volume scale and the time scale.

15. A device as defined in claim 14, wherein the label defines an axially-extending window located adjacent to the liquid volume scale allowing a user to view a liquid within the chamber and determine at least one of (i) a volume of liquid in the chamber, or (ii) a volume of liquid dispensed from the chamber, based on the liquid volume scale.

16. A device as defined in claim 1, wherein the body defines a substantially smooth, axially extending patient information surface having (i) a plurality of marking spaces for marking patient information thereon and (ii) patient information indicia associated with each marking space.

17. A device as defined in claim 16, wherein the patient information indicia includes at least one of the following: patient name, patient identification number or alphanumeric indicia, patient room number, oral contrast imaging agent added to the beverage, oral contrast imaging agent lot number and expiration date, volume of oral contrast imaging agent added to the beverage, the date the beverage and oral contrast imaging agent were mixed, the time the beverage and oral contrast imaging agent were mixed, the person that prepared the mixture, and device number when more than one device is to be consumed by a patient in a particular temporal sequence.

18. A device as defined in claim 1, wherein the liquid comprises a predetermined volume of a water soluble oral contrast imaging agent suitable for at least one of X-ray, CT and MR imaging.

19. A device as defined in claim 1, wherein the device is a bottle including a substantially cylindrical body and a neck extending upwardly from the substantially cylindrical body, the neck defining the orally-engageable opening, and the closure is releasably connected to the neck to seal the orally-engageable opening.

20. A device as defined in claim 1, in combination with a separate patient information label that is attachable to the body, is defined by a substantially flat sheet allowing a user to place the label on a substantially flat surface and write thereon, and has (i) a plurality of marking spaces for marking patient information thereon and (ii) patient information indicia associated with each marking space.

21. A device as defined in claim 20, wherein the patient information indicia includes at least one of the following: patient name, patient identification number or alphanumeric indicia, patient room number, oral contrast imaging agent added to the beverage, volume of oral contrast imaging agent added to the beverage, the date the beverage and oral contrast imaging agent were mixed, the time the beverage and oral contrast imaging agent were mixed, the person that prepared the mixture, and device number when more than one device is to be consumed by a patient in a particular temporal sequence.

22. A device as defined in claim 20, wherein (i) the body further includes thereon a substantially smooth, axially extending patient information surface including thereon a plurality of marking spaces for marking patient information thereon and patient information indicia associated with each marking space, and (ii) the patient information label is adapted for attachment to the body in a position overlying the patient information surface.

23. A device as defined in claim 22, wherein the patient information label is substantially the same size and shape as the patient information surface for substantially entirely covering the patient information surface when attached thereto.

24. A device as defined in claim 23, wherein the patient information label is an adhesive backed label that is releasably attachable to the patient information surface.

25. A device as defined in claim 1, wherein the liquid comprises a mixture of a beverage and an oral contrast agent.

26. A device as defined in claim 1, wherein the predetermined volume of head space is configured to provide space to mix the predetermined volume of oral contrast imaging agent with the liquid.

27. A device for storing a beverage, receiving an oral contrast imaging agent that is mixed with the beverage, and dispensing a resulting mixture, the device comprising:
   first means for forming a chamber and for forming an orally-engageable opening to the chamber, the first means containing a liquid filled to a first level within the chamber, and a predetermined volume of head space above the first level for receiving a predetermined volume of oral contrast imaging agent for mixture with the liquid within the chamber, thereby filling the chamber to a second level and forming the resultant mixture of liquid prior to consumption thereof by a user, wherein the predetermined volume of head space is configured so that the predetermined volume of oral contrast imaging agent provides a proper concentration in the resultant mixture of liquid for imaging;
   second means movable between a closed position for closing the orally-engageable opening and for sealing the chamber, and an open position for at least one of (i) introducing an oral contrast imaging agent into the chamber through the orally-engageable opening for mixture with a beverage in the chamber, and (ii) allowing a user to engage the orally-engageable opening and consume the mixture from the chamber through the opening, and thereby dispensing the mixture;
   a third means located on the first means below the second level for indicating a volume at a third level within the chamber below said second level and for indicating (i) a first time or (ii) a first time interval, by which a user should consume the liquid through the orally-engageable opening to the indicated third level within the first means; and
   a fourth means located on the first means below said third means for indicating a fourth level within the chamber below said third level and for indicating (i) a second time later than the first time or (ii) a second time interval, by which a user should consume the liquid through the orally-engageable opening to the indicated fourth level within the chamber,
   wherein said third means is located closer to the orally-engageable opening than said fourth means.

28. A device as defined in claim 27, wherein the first means comprises a body.

29. A device as defined in claim 28, wherein the second means comprises a closure, the third means comprises a first marking, and the fourth means comprises a second marking.

30. A device as defined in claim 27, further comprising a plurality of fifth means located on the first means and axially spaced relative to each other for indicating a respective volume of the mixture in the first means.

31. A device as defined in claim 30, wherein each fifth means comprises a graduation of a liquid volume scale.

32. A device as defined in claim 27, wherein the predetermined volume of head space is configured to provide space to mix the predetermined volume of oral contrast imaging agent with the liquid.

33. A device for storing a beverage, receiving an oral contrast imaging agent that is mixed with the beverage, and dispensing a resulting mixture, the device comprising:
   a body defining a chamber, an orally-engageable opening to the chamber, the chamber containing a liquid filled to a first level within the chamber, and a predetermined volume of head space above the first level for receiving a predetermined volume of oral contrast imaging agent for mixture with the liquid within the chamber and forming the resultant mixture prior to consumption thereof by a user, wherein the predetermined volume of head space is configured so that the predetermined volume of oral contrast imaging agent provides a proper concentration in the resultant mixture for imaging;
   a closure movable between a closed position configured to close the orally-engageable opening and seal the chamber, and an open position configured to at least one of (i) introduce the oral contrast imaging agent into the chamber through the orally-engageable opening for mixture with a beverage, and (ii) allow a user to engage the orally engageable opening and consume the resultant mixture from the chamber through the opening, and thereby dispense the resultant mixture;
   a first marking located on the body below the first level and indicating a second level within the chamber below said first level, the marking further comprising (i) a first time or (ii) a first time interval, by which a user should consume the liquid through the orally-engageable opening to the indicated second level within the chamber; and
   a second marking located on the body below the first marking and indicating a third level within the chamber below said second level, the second marking further comprising (i) a second time later than the first time or (ii) a second time interval, by which a user should consume the liquid through the orally-engageable opening to the indicated third level within the chamber,
   wherein said first marking is located closer to the orally-engageable opening than said second marking.

34. A device as defined in claim 33, further including a neck extending upwardly from the body defining the opening in fluid communication with the chamber, and the head space extends between the first level and the neck.

35. A device as defined in claim 33, wherein the predetermined volume of head space is configured to provide space to mix the predetermined volume of oral contrast imaging agent with the liquid.

* * * * *